(12) United States Patent
Fisher et al.

(10) Patent No.: US 7,207,799 B2
(45) Date of Patent: Apr. 24, 2007

(54) DENTAL PROSTHESIS SUPPORT AND METHOD

(75) Inventors: Keith S. Fisher, Orangeburg, NY (US); John Cogger, Santa Ana, CA (US); Eric R. Fisher, Nanuet, NY (US); David H. Fisher, Nanuet, NY (US); Shaan Y. Khan, Plainview, NY (US)

(73) Assignee: Instabar Technologies, LLC, Plainview, NY (US)

( * ) Notice: Subject to any disclaimer, the term of this patent is extended or adjusted under 35 U.S.C. 154(b) by 225 days.

(21) Appl. No.: 10/879,992

(22) Filed: Jun. 29, 2004

(65) Prior Publication Data

US 2005/0019729 A1 Jan. 27, 2005

Related U.S. Application Data

(60) Provisional application No. 60/484,182, filed on Jun. 30, 2003, provisional application No. 60/498,560, filed on Aug. 27, 2003.

(51) Int. Cl.
*A61C 8/00* (2006.01)
(52) U.S. Cl. .................................................. 433/172
(58) Field of Classification Search ............... 433/172, 433/173, 174
See application file for complete search history.

(56) References Cited

U.S. PATENT DOCUMENTS

| | | | | |
|---|---|---|---|---|
| 1,140,538 A | * | 5/1915 | Skinner | 433/180 |
| 3,514,858 A | * | 6/1970 | Silverman | 433/174 |
| 3,748,739 A | * | 7/1973 | Thibert | 433/173 |
| 4,129,680 A | | 12/1978 | Vines | |
| 4,225,668 A | * | 9/1980 | Bartoli | 433/176 |
| 4,269,595 A | | 5/1981 | Nemethy | |
| 4,490,112 A | * | 12/1984 | Tanaka et al. | 433/20 |
| 4,689,013 A | | 8/1987 | Lustig | |
| 4,767,328 A | * | 8/1988 | Branemark | 433/168.1 |
| 4,826,436 A | | 5/1989 | Shoher et al. | |
| 4,897,036 A | * | 1/1990 | Kesling | 433/18 |
| 4,950,162 A | | 8/1990 | Korber et al. | |
| 5,074,791 A | | 12/1991 | Shoher et al. | |
| 5,098,296 A | | 3/1992 | Cullen | |
| 5,102,337 A | | 4/1992 | Soroca | |
| 5,174,954 A | * | 12/1992 | Schaffer et al. | 420/463 |
| 5,219,286 A | * | 6/1993 | Hader | 433/172 |

(Continued)

FOREIGN PATENT DOCUMENTS

DE 38 00 367 A1 * 8/1988

(Continued)

*Primary Examiner*—Ralph A. Lewis
(74) *Attorney, Agent, or Firm*—Walker A. Hackler

(57) ABSTRACT

Dental prosthesis support apparatus includes a plurality of dental implants having self-tapping threads on a lower portion thereof for seating in a jawbone and an upper portion for enabling engagement therewith. An armature is provided having sufficient flexibility to be aligned with the jawbone and engaged along the upper portions of each of the plurality of dental implants seated in the jawbone. The armature is formed from a material enabling subsequent rigidization. The method includes installing a plurality of dental implants into a jawbone in a spaced apart relationship and thereafter removably disposing an armature onto each of the plurality of dental implants and aligning the armature with the jawbone. The armature is removed and rigidized to the jawbone alignment and thereafter affixed onto each of the implants.

19 Claims, 8 Drawing Sheets

U.S. PATENT DOCUMENTS

| | | |
|---|---|---|
| 5,302,122 A | 4/1994 | Milne |
| 5,427,906 A * | 6/1995 | Hansen ................... 433/173 |
| 5,509,933 A | 4/1996 | Davidson et al. |
| 5,516,288 A | 5/1996 | Sichler et al. |
| 5,562,448 A | 10/1996 | Mushabac |
| 5,584,695 A * | 12/1996 | Lal Sachdeva et al. ..... 433/173 |
| 5,674,070 A | 10/1997 | Fortin et al. |
| 5,775,900 A | 7/1998 | Ginsburg et al. |
| 5,885,078 A | 3/1999 | Cagna et al. |
| 6,048,204 A | 4/2000 | Klardie et al. |
| 6,116,070 A | 9/2000 | Oshida et al. |
| 6,186,790 B1 | 2/2001 | Karmaker et al. |
| 6,299,448 B1 | 10/2001 | Zdrahala et al. |
| 6,319,000 B1 | 11/2001 | Brånemark |
| 6,322,364 B1 * | 11/2001 | Oshida et al. .............. 433/173 |
| 2002/0137003 A1 | 9/2002 | Knapp |

FOREIGN PATENT DOCUMENTS

| | | |
|---|---|---|
| EP | 1 083 243 A2 | 3/2001 |
| JP | 01209059 A * | 8/1989 |

* cited by examiner

160°

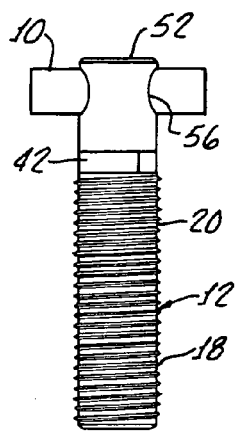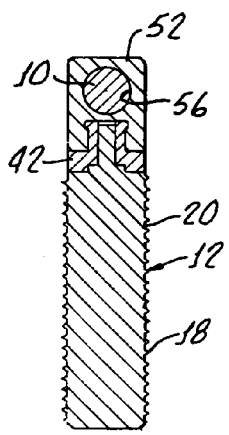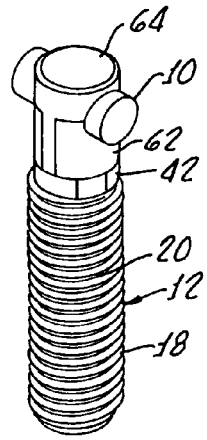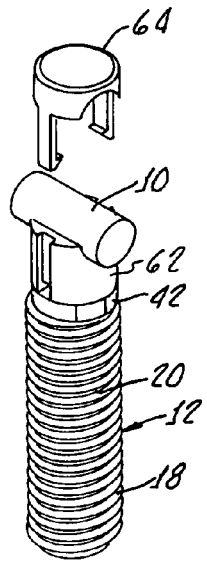
*Fig. 11.*   *Fig. 12.*   *Fig. 13.*   *Fig. 14.*
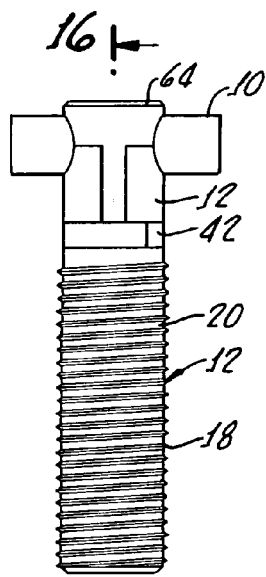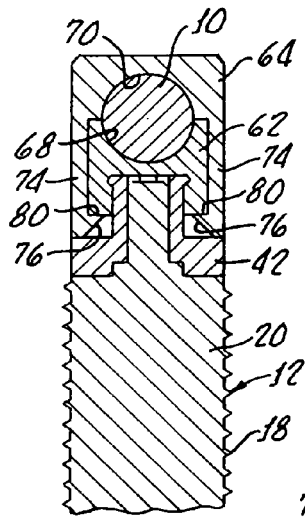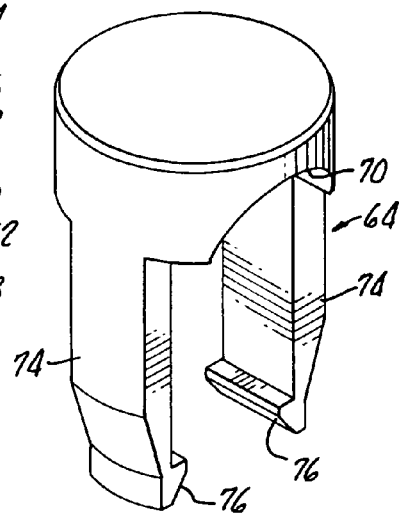
*Fig. 15.*   *Fig. 16.*   *Fig. 17.*

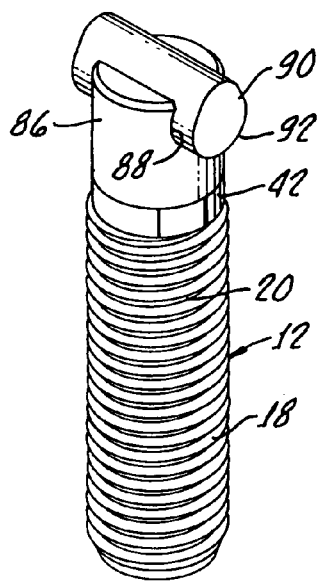
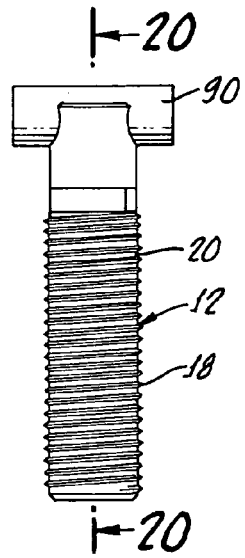
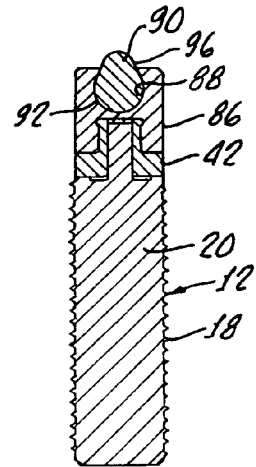
FIG. 18.    FIG. 19.    FIG. 20.
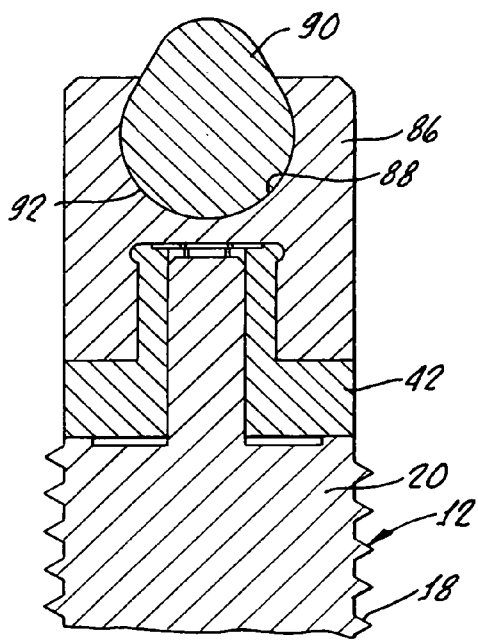
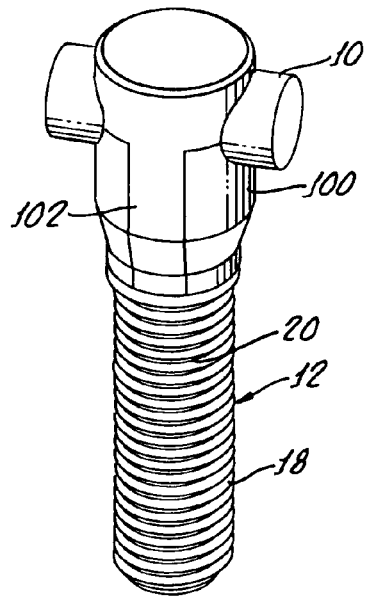
FIG. 21.    FIG. 22.

DENTAL PROSTHESIS SUPPORT AND METHOD

The present application claims priority from U.S. Provisional Application Ser. No. 60/484,182 filed Jun. 30, 2003 and Ser. No. 60/498,560 filed Aug. 27, 2003.

For patients requiring restorative dentistry in the form of dentures, there are two basic options: (a) unsupported dentures, which use adhesive compounds to attach the prosthesis to the patients' mandible; and (b) supported dentures, which use an armature, and associated bone implants, as a mechanical means of attaching the prosthesis to the patients' mandible.

The overwhelming majority of denture applications use the unsupported type of dentures, with adhesive attachment.

Supported implant dentistry relies on multiple components including implants, abutments, and prosthesis to complete a reconstructive effort. These components are deployed over a series of office visits by the patient, wherein molds are made, and specific reconstructive dentistry is applied.

The basic component of the prosthodontic system is the implant itself, a cylindrical, titanium post with self-tapping threads designed to engage the patient's jawbone. Additionally, this component contains an internal thread to capture an impression post as well as other types of cylindrical abutments.

For certain types of restorative dentistry, such as those requiring an over denture prosthesis, a bridge bar, or a connective plate, is fabricated to connect all the implants and act as an armature for the prosthesis. This plate, or armature, has significant patient-to-patient variability in its current design embodiment, and must be sent to an outside lab for processing by a technician. This is costly, and results in additional patient office visits, as well as delays associated with outsourcing.

The present invention is directed to apparatus and methods to eliminate some of these undesirable attributes such as cost and extra patient visits, by standardizing the armature, and making specific patient configuration adjustments at the point of care.

SUMMARY OF THE INVENTION

Dental prosthesis support apparatus in accordance with the present invention generally includes a plurality of preformed armatures, preferably formed Nitinol®. Each armature includes sufficient flexibility to be aligned with a jawbone and a plurality of dental implants seated therein. The plurality of preformed armatures may include four armatures which enabling alignment with of 95% of all human adult jawbones. The Nitinol® is heat treatable to rigidized the aligned armature to the aligned shape.

More particularly, the dental prosthesis support apparatus in accordance with the present invention may include a plurality of dental implants, each having self-taping threads or non-self taping threads or on a lower portion thereof for seating in a jawbone and an upper portion for enabling engagement therewith. Alternatively, the lower portion may have a cylindrical shape for press fitting into the jawbone.

Armatures are provided having sufficient flexibility to be aligned with the jawbone and engaged along the upper portions of each of the plurality of dental implants seated in the jawbone. The armatures thereafter are rigidized. In that regard, the armatures preferably formed from a shape memory alloy and most preferably formed from Nitinol®.

Still more particularly, dental prosthesis support apparatus in accordance with the present invention may include a plurality of dental implants having self-taping threads on a lower portion thereof for engaging a jawbone. An armature is provided and formed from a shape memory alloy having sufficient flexibility to be aligned with the jawbone along upper portions of each of the plurality of dental implants seated in the jawbone. The armature is thereafter rigidized by heat-treating.

A plurality of abutments may be provided for fixing the rigidized armature to each of the dental implant upper portions.

In one embodiment of the present invention, each of the dental implant upper portions and each of the abutments include threads for enabling engagement between the dental implant and a respective abutment. In addition, each abutment may include a snap hook for capturing the armature or a saddle and a nut for capturing the armature.

Alternatively, in accordance with the present invention, each abutment may include a shaped slot for receiving a complimentary shaped armature or each abutment may include a setscrew for attachment to the armature.

A method in accordance with the present invention for providing a dental support generally includes installing a plurality of dental implants into a jawbone in a spaced apart relationship and thereafter an armature is removably disposed onto each of the plurality of dental implants and the armature is aligned with the implants and the jawbone.

The aligned armature is then removed and rigidized to the aligned shape.

The rigidized armature is then fixed onto each of the implants.

Preferably, the method in accordance with the present invention includes removably disposing a shape memory alloy armature onto each of the implants and the shaped memory alloy is rigidized by heat treatment.

A method in accordance with the present invention may also include installing a plurality of dental implants onto a jawbone in a spaced apart relationship and disposing an abutment on each of the dental implants. An armature is disposed onto each of the abutments and aligned with the armature and with the jawbone. The aligned armature is then removed and rigidized to the aligned shape. The rigidized armature is then fixed to the abutments.

BRIEF DESCRIPTION OF THE DRAWINGS

The advantages and features of the present invention will be better understood by the following description when considered in conjunction with the accompanying drawings in which:

FIG. 11 is a side view of the abutment shown in FIG. 10;

FIG. 12 is a cross sectional view of the abutment and implant of FIG. 11;

FIG. 13 is a perspective view of an alternate embodiment of an abutment in which a saddle is equal in radius to the diameter of the armature and a snap hoop;

FIG. 14 is an exploded view of the abutment shown in FIG. 13;

FIG. 15 is a side view of the abutment and implant shown in FIGS. 13–14;

FIG. 16 is a cross sectional view of the abutment and implant shown in FIG. 15 taken along the line 16—16;

FIG. 17 is perspective view of the snap hoop suitable for use with armatures in accordance with the present invention;

FIG. 18 is a perspective view of an alternative embodiment of the present invention utilizing an armature and a saddle having conforming shapes for ensuring engagement;

FIG. 19 is a side view of the abutment and implant shown in FIG. 18;

FIG. 20 is a cross sectional view of the abutment and implant taken along the line 2O—2O of FIG. 19;

FIG. 21 is an enlarged view of the cross section of the armature and abutment shown in FIG. 20;

FIG. 22 is an alternative embodiment in accordance with the present invention;

DETAILED DESCRIPTION

Figure 1:
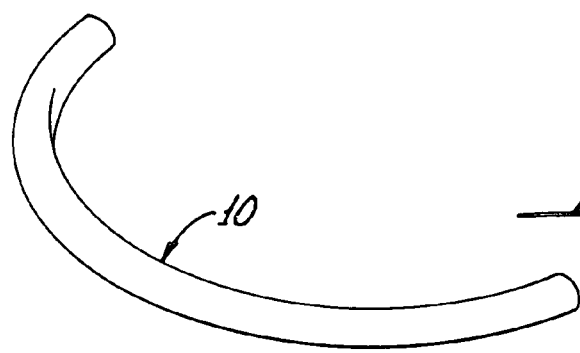
FIG. 1 shows one of a plurality, preferably four, of standardized preformed armatures.
Figure 1A:
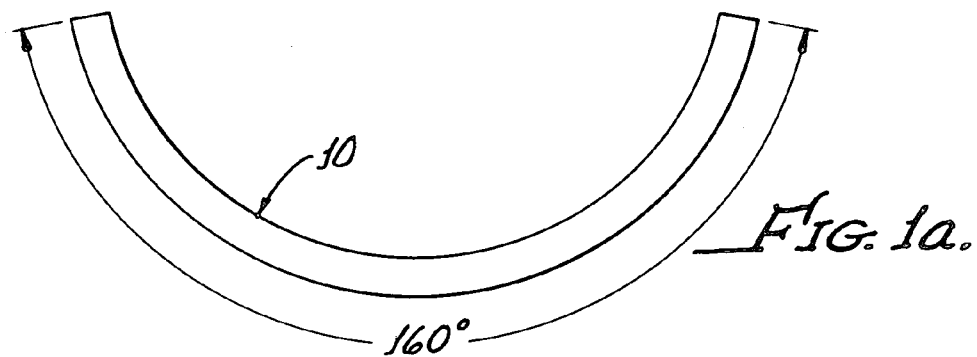
FIG. 1a is a plan view of the armature shown in FIG. 1.
Figure 1B:
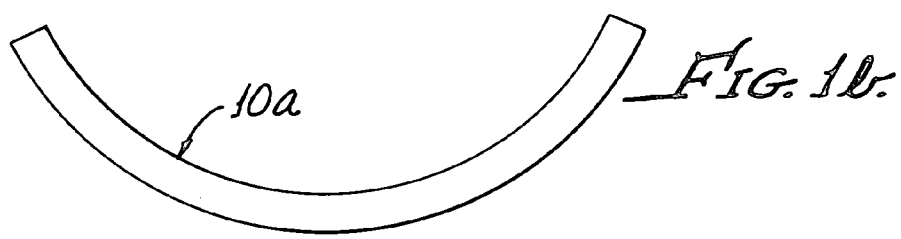
FIG. 1b–1d are plan views of three other armatures of the plurality noted hereinabove.
Figure 1C:
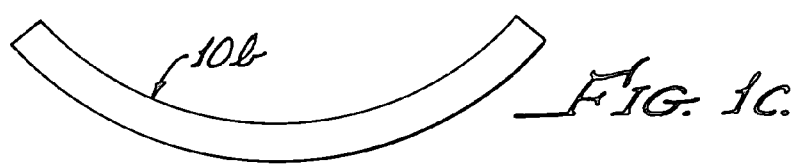
Figure 1D:
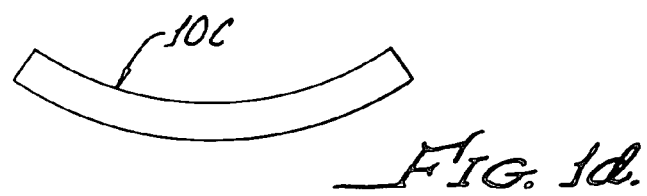

With reference to FIG. 1, there is shown a preformed armature 10 similar to three other armatures, not shown in FIG. 1, with each armature having sufficient flexibility to be aligned with a jawbone and a plurality of dental implants (not shown in FIG. 1) seated therein.

The plurality of preformed armatures 10, 10a, 10b, 10c are selected for fitting up to 95% of all human adult jawbones, see FIGS. 1a–1d.

Importantly, the armature 10 is formed from a material enabling subsequent rigidization.

Preferably, the armatures 10–10c are formed from a shape memory alloy such as Nitinol® which consists of approximately 50% titanium and 50% nickel. However, it is to be appreciated that the present invention is meant to include other materials heretofore and hereinafter developed which may have the same characteristics of Nitinol®.

These characteristics include a high adjustability in 6 degrees of freedom, translation in X, Y, and Z, and rotation around each axis. Accordingly, the armatures 10–10c are perfectly customized to a specific patient without expensive machining or casting. In addition, after rigidization and the armature is complete, it has a very high strength properties and able to resist normal jaw forces with an adequate safety margin. No residual forces or pre-stress is applied to the patients' 'jaw after the implant is complete. Reference hereinafter to armature 10 is meant to include reference to armatures 10a–10c.

The process to convert the un-yield armature to a high strength custom contour armature is well known for shape and memory alloys and includes the steps of:

Shape memory cycling (Cool->Deform->Heat->Repeat),
Pseudo elastic cycling (Load->Unload->Repeat);
Combine shape memory and pseudo elastic cycling; and
Constrain temperature cycling of deformed martensite.

As is well known, thermo cycling occurs at very distinct temperatures which can be determined experimentally and the exact alloy constitution is determined to optimize the transformation temperature.

Figure 3:
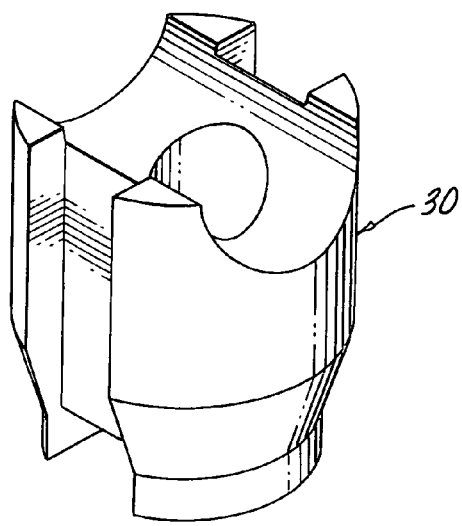
FIG. 3 is a perspective view of the saddle abutment illustrated in FIG. 3.

In accordance with the method of the present invention, an oral surgeon implants a plurality of conventional Ti implants 12 into a mandible, or jawbone, a jawbone representation 16 being shown in FIG. 3.

Figure 2:
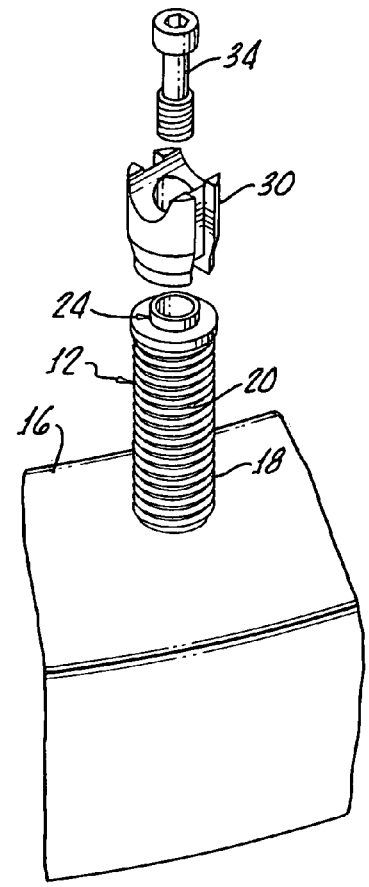
FIG. 2 illustrates the installation of a saddle abutment onto the implant utilizing a long axis screw.

As illustrated in FIG. 2, the implant 12 includes self-tapping screws 18 an a lower portion 20 thereof. Alternatively, the screws may be non-self tapping or the lower portion may be of a shape for enabling press fitting of the implant 12 into the jawbone 16.

The conformal armature 10 in accordance with the present invention is able to follow geometric variations of implant 12 placement. That is, a centerline 22 of the implant 12 when seated in the jawbone 16 may be skewed into orthogonal directions with reference to a normal 26 extending from the jawbone 16, as will be hereinafter described in greater detail. A threaded upper portion 24 enables engagement with the implant 12.

Figure 4:
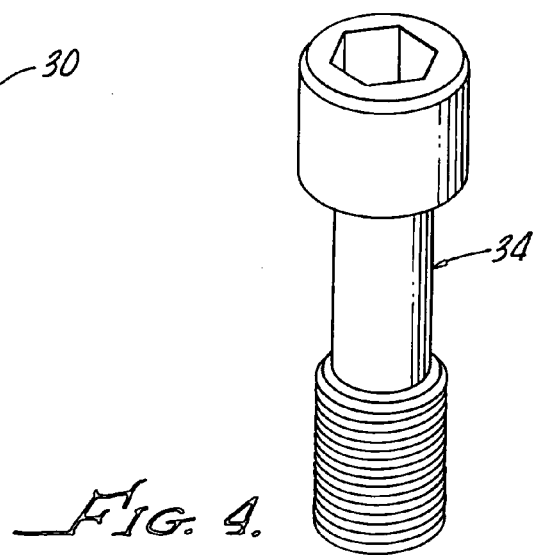
FIG. 4 is a perspective view of the long axis screw illustrated in FIG. 3.

As also illustrated in FIG. 2, a saddle type abutment may be threaded onto the implant 12 through the use of a long axis screw 34, respective views of the saddle abutment 20 along axis being shown in FIGS. 3 and 4 respectively.

Figure 5:
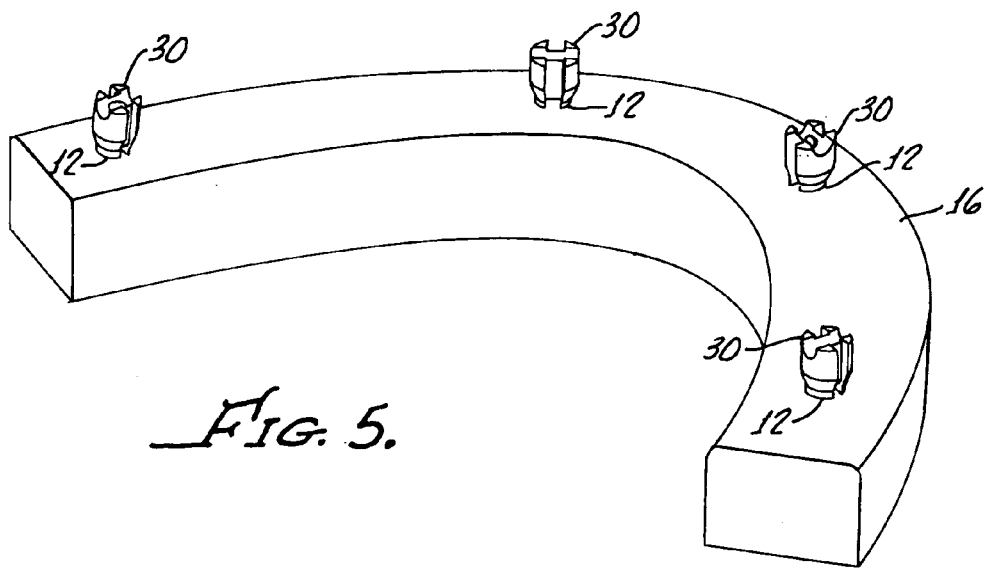
FIG. 5 is a perspective view of four implants in a spaced apart-seated relationship in a lower jaw representation.

As depicted in FIG. 5, a plurality of implants 12 with attached abutments 30 are shown in a spaced apart relationship in the jawbone 16, the four implants 12 shown in the lower jawbone 16 illustrate seating with four different heights, with one shown with an exaggerated off axis configuration to illustrate the flexibility of the apparatus and method in accordance with the present invention. In addition, the center-to-center spacing of the implants 12 is unequal and, of course, different from patient to patient which is accommodated by the method and apparatus of the present invention.

Figure 6:
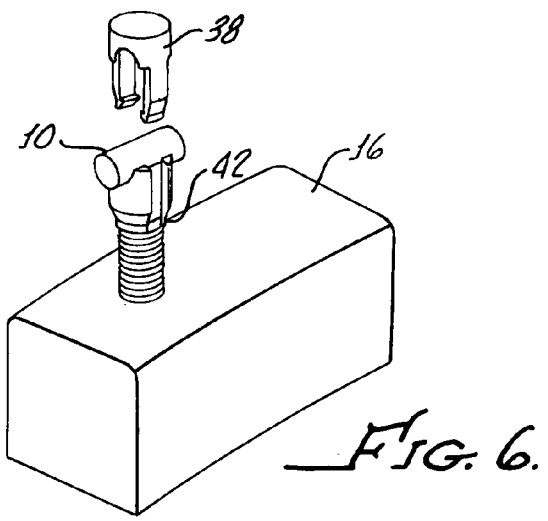
FIG. 6 is a perspective view of an armature aligned in the saddle shown in FIG. 3 along with a snap hoop collar for fixing the armature to the implant via the abutment.
Figure 7:
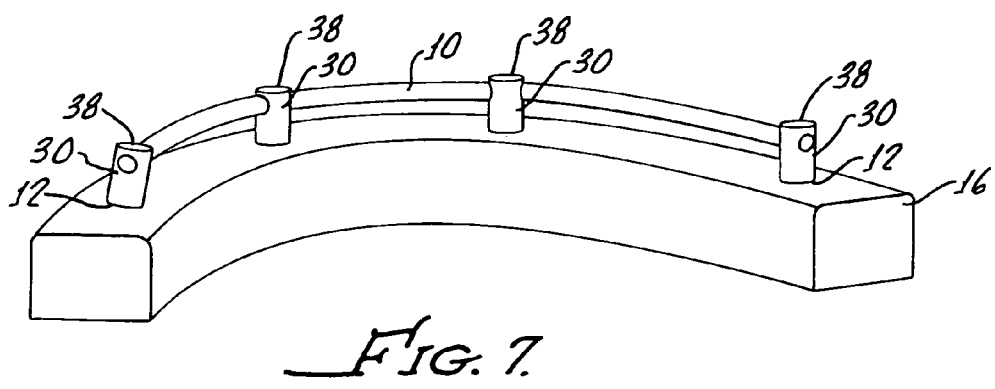
FIG. 7 illustrates the armature installed in the four implants illustrated in FIG. 5 also illustrating conformal fitting of the armature despite severe off axis conditions of the spaced apart implants.

As shown in FIGS. 6 and 7, the method in accordance with the present invention includes removably disposing the armature 10 onto each of the implants 10 and abutments 30 and aligning the armature 10 with the jawbone 16 curvature and the implants 12.

Figure 8:
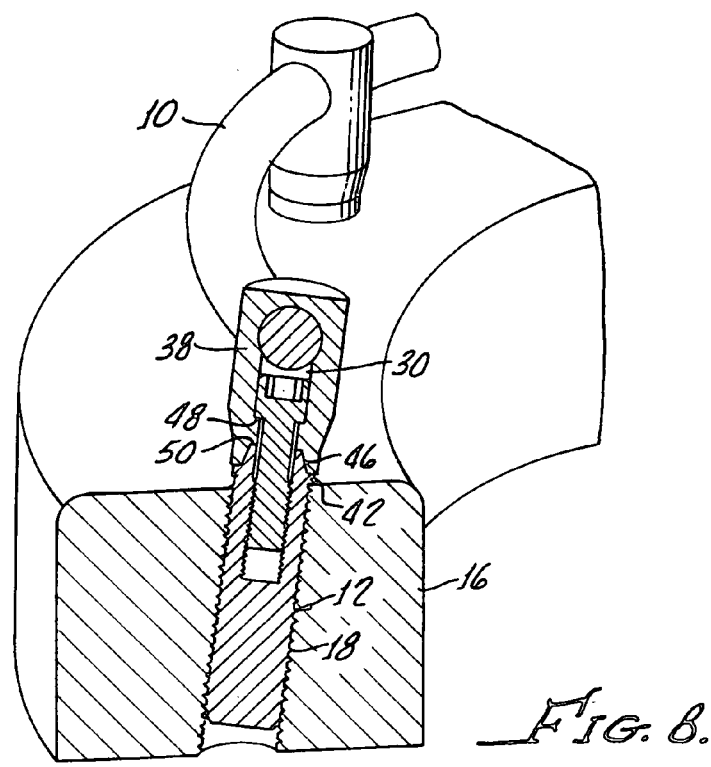
FIG. 8 is a cross sectional view of one of the implants shown in FIG. 7 also illustrating a radial abutment collar for providing an upward force to lock abating dove-tail surfaces.
Figure 9:
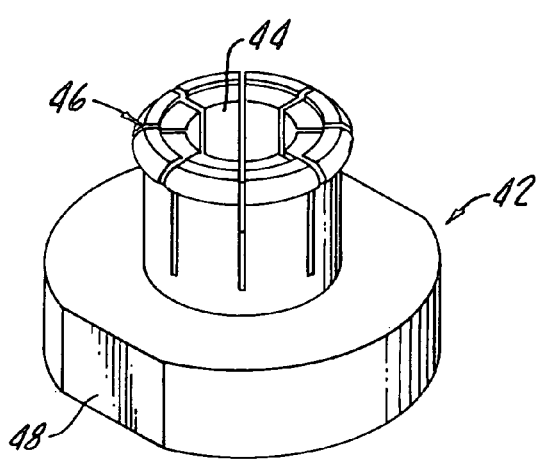
FIG. 9 is a perspective view of the captive nut shown in FIG. 8.

After alignment, the armature 10 is removed and rigidized, preferably by heat-treating when a Nitinol® armature is utilized. Thereafter, the rigidized armature 10 is fixed on to the implants 12 and abutments 30 utilizing, for example, a snap hook, or collar, 38, see FIGS. 6 and 8.

Figure 10:
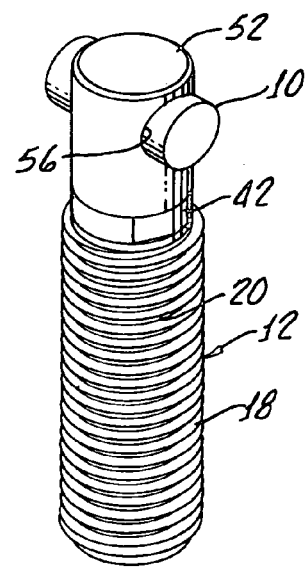
FIG. 10 is one embodiment of an abutment in accordance with the present invention including a hole therethrough of the same diameter of the armature along with a captive nut.

A captive nut 42, most clearly shown in FIG. 10, having internal threads 44, is provided for engaging the implant with an upper collet portion 46 and is rotatable through wrench flats 48. When tightened, the collet 46 provides an upward force to lock meeting dovetail surfaces 48, 50, see FIG. 8.

The hereinabove described method in accordance with the present invention eliminates the processing of a prior art armatures (not shown) by using sand casting, investment casting, lost wax casting, laser machining.

In addition, because of the onsite processing of the armature, reduced number of office visits are possible which concomitantly reduces the cost of the procedure. In addition, a shorter time span is necessary to completely the reconstructive dentistry and the use of the standardized preformed armatures 10 to three or more pre-forms 10–10c enable the fitting of 95% of adult jawbones.

Method in accordance with the present invention also enables the fitting of the armature 10 to implants having various displaced axes from the jawbone 16 and the rotation of the armature further provides for accommodating implants which are not perfectly seated in an aligned relationship with one another in the jawbone. A number of implants 12 may be utilized with the minimum being two.

While the implants 12 may be configured for direct attachment thereto, it is preferable that some type of abutment 30 be utilized. A number of variations may be utilized in accordance with the present invention.

For example, as shown in FIGS. 10–12, an abutment 52 may include an aperture 56 therethrough having a diameter for receiving the armature 10. Prior to forming, the abutments 52 are loose as installed over the armature 10 and when slid over the armature 10 allow for 360° rotation around the armature centerline. The capture nut 42 allows tightening of the abutment to the implant 12. At this point, the armature 10 is annealed, or elastic, having flexibility for enabling alignment with the jawbone, not shown, in FIGS. 10–12, with the capture nut 42 establishing a remaining degrees of freedom at each implant 12 location of the jawbone 16.

After heat treatment, the armature 10 will be inelastic and removal from implants will impart temporary stress or distortion, however this will revert to 0 when the armature 10 is seated on the implant 12 through tightening of the capture nut 42. Thereafter, no residual stress will incur. With reference to FIGS. 13–16, there is shown an alternative embodiment of an abutment 62 and snap hoop 64.

The abutment 62 includes a saddle 68 having a radius equal to the diameter of the armature 10. The saddle 68 has slightly less than one-half of the diameter of the armature 10 to allow ease of installation of the armature in a patients' mouth.

The snap hoop 64 includes a curvature 70, which is slightly greater than one-half of the bar diameter for securely clamping the armature against the lower saddle 68. The snap hoop 64 is snapped over the armature 10 just prior to installation in the patient.

Similar to the embodiment 52, the capture nut 42 operates for tightening the bar 10 to the abutment 62 and implant 10 by rotation. FIG. 17 is an enlarged perspective view of the snap hoop 64 showing depending arms 74 and hooks 76 for engaging surfaces 80 of the abutment 62.

With reference to FIGS. 18–20, there is shown yet another embodiment of an abutment 86, which includes a shaped slot 88 for receiving an armature 90 having a complimentary shaped portion 92. In this embodiment, the bar 90 cross-section is eccentric with a radius extending slightly above the centerline of the armature 90 and tangent sides 96 forming a decreasing angle.

This feature enables the armature 90 design to omit any abutment geometry extending above the top of the armature by utilizing the complimentary shapes to secure the bar to the abutment 86. As hereinabove discussed, the capture nut 42 allows tightening of the assembly without influencing orientation of the armature 90 centerline.

Additionally, tightening of the capture nut 42 acts to clamp as sealing surface of the slot, or saddle, 88 against the implant 12, which acts to backup the rigidity of the saddle aperture 88 preventing the abutment, or saddle, from further deflecting one intentional is applied.

Figure 23:
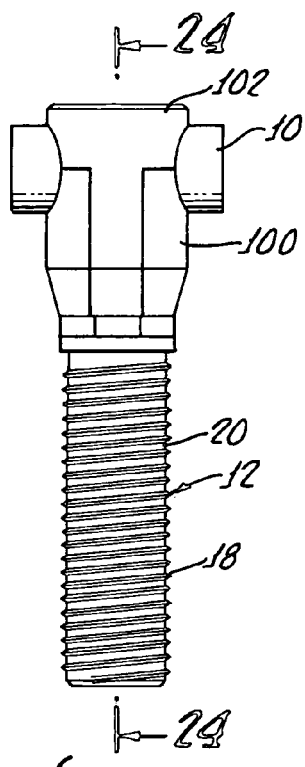
FIG. 23 is a side view of the embodiment shown in FIG. 22.
Figure 24:
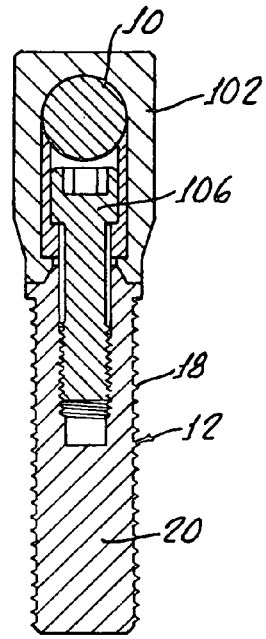
FIG. 24 is a cross sectional view taken along the line 24—24 of FIG. 23.

FIGS. 22–24 show an alternative abutment 100 similar to the abutment 62 shown in FIGS. 13–16. In this embodiment, a snap hoop 102 is provided. The abutment, or saddle, 100 includes a radius equal to the same diameter of the armature 10, both having a circular cross section. The saddle 100 has a slightly less than one-half of the diameter of the bar below a mating surface to allow ease of installation of the bar in the patients' mouth and the snap hoop 102 has slightly greater than one-half of the bar diameter and securely the armature 10 against the abutment 100. The snap hoop 102 is snapped over the armature 10 just prior to installation in the patient. It should be appreciated that the armature 10 may have a diameter of approximately 3 mm.

In this embodiment 100, as shown in FIG. 24, the abutment 102 is attached with a long axis screw 106 which threads directly into the implant 12. This design enables the abutment 102 to be fixed to the implant 12 before the armature 10 is installed. Thereafter, the snap hoop 102 is installed.

Figure 25:
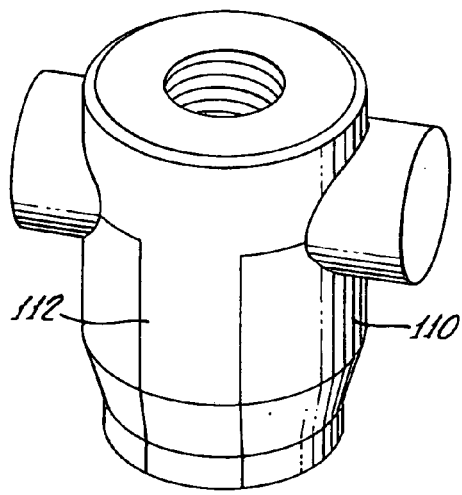
FIG. 25 is a exploded perspective view yet of another embodiment of an abutment in accordance with the present invention utilizing a setscrew.
Figures 26, 27:
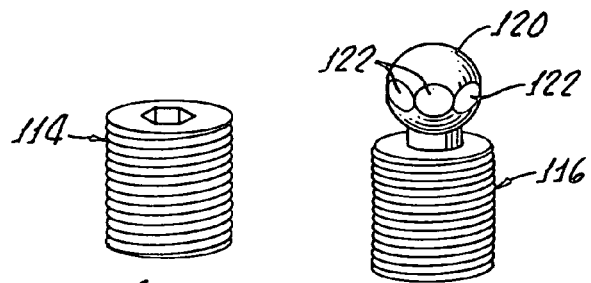
FIG. 26 is a view of a setscrew for use with the embodiment shown in FIG. 27.
FIG. 27 is a view of an alternative embodiment of a setscrew for use with the embodiment shown in FIG 25.
Figures 28, 29:
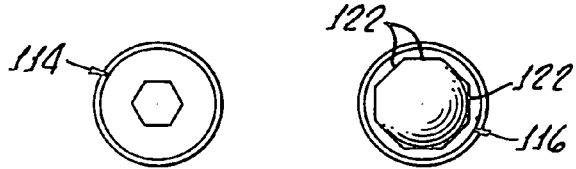
FIG. 28 is a top view of the setscrew shown in FIG. 26.
FIG. 29 is a top view of the setscrew shown in FIG. 27.

Yet another embodiment of an abutment 110 is shown in FIG. 25 along with a snap hoop 112. In this embodiment, the abutment and snap hoop 12 are fixed directly to the implant (not shown) through the use of a nut screw 114, 116 rotatable through the use of recess 114 of a shape enabling insertion of an Allen-type wrench (or the like) or a head 120 having flatten sides 122 for engagement through the use of a box wrench, or the like (not shown), see FIGS. 27–30.

Figure 30:
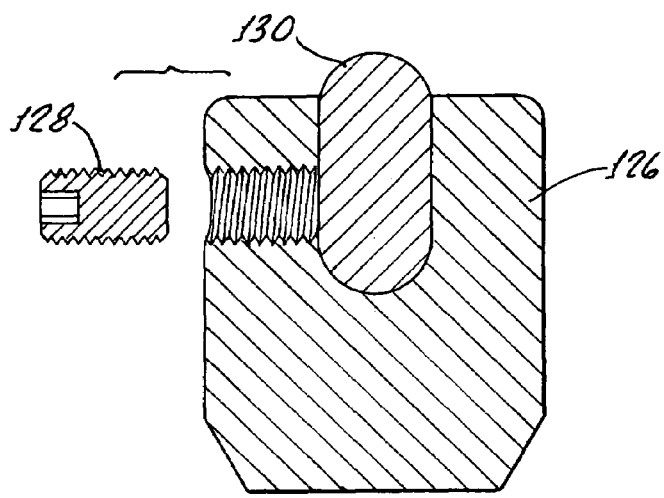
FIG. 30 is a side view representative of an alternative abutment and armature in accordance with the present invention showing a side setscrew.

FIG. 30 illustrates another embodiment abutment 126 utilizing a setscrew 128 for fastening to a rounded hexagonally shaped armature 130.

Figure 31:
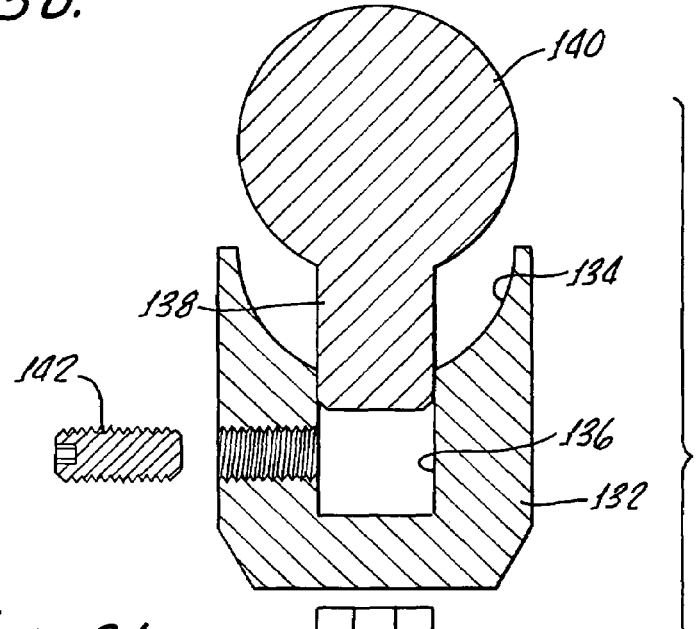
FIG. 31 is yet another abutment embodiment and armature utilizing a side setscrew for fixing the armature via a depending portion of the abutment.

Yet another embodiment of an abutment 132 is shown in FIG. 31 utilizing a saddle 134 having a depending groove 136 for receiving a depending portion 138 of an armature 140 which is secured therein by a setscrew 142.

Although there has been hereinabove described a specific dental prosthesis support and method in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. Dental prosthesis support apparatus comprising:
   a plurality of dental implants having a lower portion thereof for seating in a jawbone and an upper portion for enabling engagement therewith; and
   an armature having sufficient flexibility to be aligned with said jawbone, and engaged along the upper portions of each of said plurality of dental implants when seated in said jawbone, said armature being formed from a material enabling subsequent rigidization.

2. The dental prosthesis support apparatus according to claim 1 wherein said armature is formed from a shape memory alloy.

3. The dental prosthesis support according to claim 2 wherein said shape memory alloy comprises Nitinol.

4. The dental prosthesis support apparatus according to claim 1 wherein each dental implant includes a snap hoop collar for capturing said armature.

5. The dental prosthesis support apparatus according to claim 1 wherein each dental implant includes a saddle and a nut for capturing said armature.

6. The dental prosthesis support apparatus according to claim 1 wherein each dental implant includes a shaped slot for receiving a complimentary shaped armature.

7. The dental prosthesis support apparatus according to claim 1 wherein each dental implant includes a setscrew for attachment to the armature.

8. Dental prosthesis support apparatus comprising:
   a plurality of dental implants having a lower portion thereof for engaging a jawbone;
   an armature formed from a shape memory alloy having sufficient flexibility to be aligned with said jawbone, along upper portions of each of said plurality of dental implants when seated in said jawbone, and thereafter rigidized by heat treating; and
   a plurality of abutments for fixing the rigidized armature to each of the dental implant upper portions.

9. The dental prosthesis support apparatus according to claim 8 wherein each of the dental implant upper portions and each of said abutments include threads for enabling engagement between end dental implant and a respective abutment.

10. The dental prosthesis support apparatus according to claim 8 wherein each abutment includes a snap hoop for capturing said armature.

11. The dental prosthesis support apparatus according to claim 8 wherein each abutment includes a saddle and a nut for capturing said armature.

12. The dental prosthesis support apparatus according to claim 8 wherein each abutment includes a shaped slot for receiving a complimentary shaped armature.

13. The dental prosthesis support apparatus according to claim 8 wherein each abutment includes a nut screw for attachment to the armature.

14. A method for providing a denture support comprising:
    installing a plurality of dental implants into a jawbone in a spaced apart relationship;
    removably disposing a armature onto each of said plurality of dental implant and aligning the armature with a jawbone;
    removing the aligned armature;
    rigidizing the armature to the jawbone alignment; and
    fixing the rigidized armature onto each of the implants.

15. The method according to claim 14 wherein removably disposing the armature includes removably disposing a shape memory alloy armature onto each of the implants.

16. The method according to claim 15 wherein the rigidizing the armature includes heat-treating the armature.

17. A method for providing a denture support comprising:
    installing a plurality of dental implants into a jawbone in a spaced apart relationship;
    disposing an abutment on each of said dental implants;
    disposing an armature onto each of the abutments and aligning the armature with said jawbone;
    removing the aligned armature;
    rigidizing the armature to the jawbone alignment; and
    fixing the rigidized armature to the abutment.

18. The method according to claim 17 wherein disposing the armature includes disposing a shape memory alloy armature into each of the abutments.

19. The method according to claim 18 wherein rigidizing the armature includes heat-treating the armature.

* * * * *